United States Patent [19]

Roth

[11] 4,058,626

[45] Nov. 15, 1977

[54] COMPOSITION AND METHOD FOR KILLING SNAILS AND SLUGS

[75] Inventor: Willy Roth, Strengelbach, Switzerland

[73] Assignee: Hoffmann-La Roche Inc., Nutley, N.J.

[21] Appl. No.: 726,096

[22] Filed: Sept. 24, 1976

[30] Foreign Application Priority Data

Sept. 29, 1975 Switzerland .................. 12585/75

[51] Int. Cl.² .................. A01N 9/24; C07C 87/68
[52] U.S. Cl. .................. 424/333; 424/330; 560/32

[58] Field of Search .................. 424/300, 330, 82; 260/471 C, 472

[56] References Cited

FOREIGN PATENT DOCUMENTS 7,000,207  12/1971  France .................. 424/82
400,122    4/1966   Switzerland .................. 556/33

Primary Examiner—Dale R. Ore
Attorney, Agent, or Firm—Samuel L. Welt; Bernard S. Leon; William M. Farley

[57] ABSTRACT

Compositions for killing slugs and snails, containing as the essential active ingredient metaldehyde and as an organoleptic denaturant benzyldiethyl-(2,6-xylylcarbamoylmethyl)-ammonium benzoate, are disclosed.

10 Claims, No Drawings

COMPOSITION AND METHOD FOR KILLING SNAILS AND SLUGS

DESCRIPTION OF THE INVENTION

This invention relates to toxic, pesticidal compositions for killing slugs and snails, containing as the active ingredient metaldehyde and as organoleptic denaturant benzyldiethyl-(2,6-xylycarbamoylmethyl)-ammonium benzoate. This invention is also concerned with a method for protecting growing plants against attack by slugs and snails by means of said compositions.

The usual compositions used to kill slugs and snails are sufficient toxicity to be dangerous to humans. For example, children, out of curiosity, and adults, because of an error, may eat such compositions and may thereby suffer damage to health and perhaps death. In order to avoid this possibility, an organoleptic denaturant is incorporated in the compositions provided by this invention.

The compositions provided by this invention can contain other additives and/or carriers, the nature thereof depending on the precise nature of the specific composition, the site of its use and the method of application. Additives having a certain degree of toxicity, phytotoxicity, odor or staining, or coloring can be tolerated. Accordingly, there can be used toxic, phytotoxic, odor-imparting, stain-forming, coloring carriers and/or diluents. Generally, however, it is preferred that the additives and/or diluents be non-toxic, non-phytotoxic, odorless, non-staining and non-coloring so that the compositions containing them have as wide an application as possible.

In addition, conventional slug and snail baits can be incorporated into the compositions of this invention. Suitable baits for slugs and snails are products from the milling, dairy and/or brewing industry. Cereals and/or proteins are preferred preferreds baits. Particularly preferred baits are feed-meal, bran, casein, malt husks, dried brewer's yeast, lyophilized beer, meat-meal, blood albumin and extracts of meat, yeasts, beer and the like.

Suitable additives to the compositions of this invention which are conventionally used in compositions for killing slugs and snails are inert fillers such as, for example, chalk, kaolin and silicic acids; antimicrobial agents such as, for example, dehydracetic acid, sorbic acid, alkali metal and alkaline earth metal salts of sorbic acid, 2,2-dihydroxy-5,5'-dichlorodiphenylmethane and the like; pigments suitable as visual discolorants such as, for example iron oxide, $Fe_4[Fe(CN)_6]_3$ (Berlin blue), phthalocyanins and the like. When a colorant is used with the compositions of this invention, it is preferred to make the coloring irregular rather than homogeneous. Blue color shades are preferred. The amounts of the additives incorporated into the compositions of this invention depend to some extent on the formulators needs.

The compositions provided by this invention can be in finely divided particulate form, but they are preferably in the form of granules having a particle size of from about 1 mm to 5 mm. The granules are each substantially identical in composition and contain all the ingredients of the slug and snail killing compositions of this invention. The granules are made by initially preparing a powder composition which can subsequently be granulated in a suitable apparatus, where required, with the addition of water. The powder compositions can also contain agents which improve the flow of the powder during mixing and granulating; for examples, finely divided silicon dioxide such as is commercially available, for example, under the trade names "Silicagel", "Neosyl" or "Acrosyl".

The ratio of benzyldiethyl-(2,6-xylylcarbamoylmethyl)-ammonium benzoate and metaldehyde in the compositions of this invention can vary within wide limits. However, the metaldehyde is preferably present in a larger amount by weight than the benzyldiethyl-(2,6-xylylcarbamoylmethyl)-ammonium benzoate; for example, the compositions may preferably contain about 1 to 10 parts by weight of metaldehyde and about 0.005 to 0.5 parts by weight of benzyldiethyl-(2,6-xylylcarbamoylmethyl)-ammonium benzoate. The relative amounts of essential ingredients present in the composition are preferably about 0.002 to about 0.01 part by weight benzyldiethyl-(2,6-xylylcarbamoylmethyl)-ammonium benzoate per part by weight metaldehyde. The baits are present in the composition in an amount of about 1-99 parts by weight, preferably about 1 to 75 parts by weight and more preferably about 50 to 70 parts by weight.

The amount of non-bait additives when present in the compositions of this invention are preferably present in amounts from about 17 to about 95 parts by weight. For example, in a composition containing 0.01 to 0.05 parts by weight benzyldiethyl-(2,6-xylylcarbamoylmethyl)-ammonium benzoate, 3 to 7 parts by weight of metaldehyde, and 1 to 7 parts by weight of bait, there is present 17.95 to 95.94 parts by weight of non-bait additives. As another example, a composition containing 0.01 to 0.02 parts by weight of benzyldiethyl-(2,6-xylylcarbamoylmethyl)-ammonium benzoate and 6 to 7 parts weight metaldehyde contains 5 to 70 parts by weight of bait and additives.

The compositions provided by this invention have wide applicability in horticulture, agriculture and forestry. They are used to protect growing plants against damage and devastation by slugs and snails.

The compositions provided by this invention can be used in varying amounts. However, they are conveniently used in an amount of from about 30 to 200 g/acre, preferably 70 to 100 g/acre, in agriculture and farming. In domestic gardens, greenhouses and open-air beds, approximately 20 grains (granules) per square meter are generally used, the diameter of these grains being approximately 3.5 mm.

The compositions of this invention can be applied by conventional dusting or spraying the site to be protected using conventional vehicles suitable for such methods of application. The compositions can also be applied by manual application to the site to be protected.

The following Examples illustrate the invention.

EXAMPLE 1

The ingredients listed hereinafter are mixed with one another in the ground form, or are ground with one another, in the amounts indicated (parts by weight).

| | |
|---|---:|
| Metaldehyde | 4,000 |
| Benzyldiethyl-(2,6-xylylcarbamoylmethyl)-ammonium benzoate | 25 |
| 2,2-Dihydroxy-5,5'-dichlorodiphenylmethane | 400 |
| Feed-meal | 32,700 |
| Bran | 25,000 |
| Chalk | 30,325 |
| Berlin Blue | 500 |

-continued

| | |
|---|---|
| Casein | 4,000 |

3,000 Parts by weight of water are added to the resulting powder and the mixture is granulated in a conventional granulating apparatus.

EXAMPLE 2

The ingredients listed hereinafter are mixed with one another in the ground from, or are ground with one another, in the amounts indicated (parts by weight).

| | |
|---|---|
| Metaldehyde | 5,000 |
| Benzyldiethyl-(2,6-xylylcarbamoylmethyl)-ammonium benzoate | 12 |
| Potassium sorbate | 500 |
| Feed-yeast | 29,375 |
| Bran | 25,000 |
| Kaolin | 37,413 |
| Cu phthalocyanin | 200 |
| Casein | 4,000 |

3,500 Parts by weight of water are added to the resulting powder and the mixture is granulated in a conventional granulating apparatus.

EXAMPLE 3

The ingredients listed hereinafter are mixed with one another in the ground form, or are ground with one another, in the amounts indicated (parts by weight).

| | |
|---|---|
| Metaldehyde | 6,000 |
| Benzyldiethyl-(2,6-xylylcarbamoylmethyl)-ammonium benzoate | 50 |
| Dehydracetic acid | 350 |
| Blood albumin | 40,000 |
| Bran | 30,000 |
| Chalk | 14,500 |
| Phthalocyanin | 100 |
| Casein | 4,000 |

5,000 Parts by weight of water are added to the resulting powder and the mixture is granulated in a conventional granulating apparatus.

EXAMPLE 4

The ingredients listed hereinafter are mixed with one another in the ground form, or are ground with one another, in the amounts indicated (parts by weight).

| | |
|---|---|
| Metaldehyde | 6,000 |
| Sorbic acid | 1,000 |
| Malt husks | 25,000 |
| Bran | 24,000 |
| Kaolin | 35,685 |
| Berlin blue | 300 |
| Casein | 4,000 |

4,000 Parts by weight of water are added to the resulting powder and the mixture is granulated in a conventional granulating apparatus. The obtained granules are given in a mixing apparatus and are sprayed uniformely with a solution of 0.015 parts by weight in 2.5 parts by weight of water. The water is then removed by evaporation.

I claim:

1. A composition toxic to snails and slugs which comprises an amount of metaldehyde which is effective as the active toxic ingredient and an amount of benzyldiethyl-(2,6-xylylcarbamoylmethyl)-ammonium benzoate which is effective as the organoleptic denaturant.

2. The composition of claim 1 containing about 1 to 10 parts by weight metaldehyde and about 0.005 to 0.5 parts by weight benzyldiethyl-(2,6-xylylcarbamoylmethyl)-ammonium benzoate.

3. The composition of claim 2 containing for each part by weight of metaldehyde about 0.002 to 0.01 part by weight of benzyldiethyl-(2,6-xylylcarbamoylmethyl)-ammonium benzoate.

4. The composition of claim 1 containing about 1 to 99 parts by weight of a snail and slug bait.

5. The composition of claim 1 containing an antimicrobial agen.

6. The composition of claim 1 containing a dye.

7. The composition of claim 1 containing 0.01 to 0.05 parts by weight of benzyldiethyl-(2,6-xylylcarbamoylmethyl)-ammonium benzoate, 3 to 7 parts by weight of metaldehyde, 1 to 7 parts by weight of bait and 17.95 parts by weight of additive.

8. The composition of claim 1 containing 0.01 to 0.02 parts by weight of benzyldiethyl-(2,6-xylylcarbamoylmethyl)-ammonium benzoate, 6 to 7 parts by weight of metaldehyde and 5 to 70 parts by weight of bait and additive.

9. A method of killing slugs and snails which consists of applying to the site to be protected sufficient amount of the composition of claim 1 to kill slugs and snails.

10. The method of claim 9 wherein the site to be protected is growing plants.

* * * * *